(12) United States Patent
Reutelingsperger et al.

(10) Patent No.: US 8,658,768 B2
(45) Date of Patent: Feb. 25, 2014

(54) METHOD FOR ENHANCING PHAGOCYTOSIS OF PHOSPHATIDYLSERINE-EXPOSING CELLS

(75) Inventors: Christiaan Peter Maria Reutelingsperger, Maastricht (NL); Peter Jozef Jacobus Moonen, Susteren (NL); Adriaan Thomas Vermaire, Kattendijke (NL)

(73) Assignee: Mosamedix B.V., Kattendijke (NL)

( * ) Notice: Subject to any disclaimer, the term of this patent is extended or adjusted under 35 U.S.C. 154(b) by 0 days.

(21) Appl. No.: 13/376,090

(22) PCT Filed: Jun. 3, 2010

(86) PCT No.: PCT/NL2010/050334
§ 371 (c)(1), (2), (4) Date: Dec. 2, 2011

(87) PCT Pub. No.: WO2010/140886
PCT Pub. Date: Dec. 9, 2010

(65) Prior Publication Data
US 2012/0094895 A1  Apr. 19, 2012

(30) Foreign Application Priority Data
Jun. 3, 2009  (EP) ..................... 09161791

(51) Int. Cl.
*C07K 14/00* (2006.01)
*A61P 37/00* (2006.01)

(52) U.S. Cl.
USPC ........... 530/350; 514/12.2; 514/16.6; 514/1.1

(58) Field of Classification Search
None
See application file for complete search history.

(56) References Cited

U.S. PATENT DOCUMENTS 8,133,971 B2 * 3/2012 Lee et al. ............. 530/300

FOREIGN PATENT DOCUMENTS

WO  WO 2005/019429 A2  3/2005
WO  WO-2006/003488 A2  1/2006
WO  WO-2007/069895 A1  6/2007

OTHER PUBLICATIONS

Huber et al.—The crystal and molecular structure of human annexin V, an anticoagulant protein that binds to calcium and membranes, EMBO J. 9-3867-3874, 1990.*
van Genderen et al. (Extracellular annexin A5: Functions of phosphatidylserine-binding and two-dimensional crystallization, Biochim. Biophys. Acta, 1738, 953-963, 2008.*
Berendes et al., Structure—Function analysis of the Ion-channel selectivity filter in human Annexin V—Science, 262, 427-430,1993.*
Wu et al. ,Phosphatidylserine recognition by phagocytes: a view to a kill, Trends in Cell Biol., 16, 189-197, 2006.*
Anuradha, et al. "RGD peptide-induced apoptosis in human leukemia HL-60 cells requires caspase-3 activation," Cell Biology and Toxicology, 2000, vol. 16, pp. 275-283, XP-002973675.
Asano, et al., "Masking of Phosphatidylserine Inhibits Apoptotic Cell Engulfment and Induces Autoantibody Production in Mice," Journal of Experimental Medicine, 2004, vol. 200, No. 4, pp. 459-467.
Bérat, et al., "Peptide-presenting two-dimensional protein matrix on supported lipid bilayers: An efficient platform for cell adhesion," Biointerphrases, 2007, vol. 2, No. 4, pp. 165-172, XP-002545056.
Gardai, et al., "Cell-Surface Calreticulin Initiates Clearance of Viable or Apoptotic Cells through trans-Activation of LPR on the Phagocyte," Cell, 2005, vol. 123, pp. 321-334.
Hodge, et al., "Azithromycin Improves Macrophage Phagocytic Function and Expression of Mannose Receptor in Chronic Obstructive Pulmonary Disease," American Journal of Respiratory and Critical Care Medicine 2008, vol. 178, pp. 139-148.
Hodge, et al., "Smoking Alters Alveolar Macrophage Recognition and Phagocytic Ability: Implications in Chronic Obstructive Pulmonary Disease," American Journal of Respiratory Cell and Molecular Biology, 2007, vol. 37, pp. 748-755.
Kenis, et al., "Annexin A5 inhibits engulfment through internalization of PS-expressing cell membrane patches," Experimental Cell Research, 2006, vol. 312, No. 6, pp. 719-726, XP005326782.
Kuijpers, et al., "Preparation and Evaluation of Glycosylated Arginine-Glycine-Aspartate (RGD) Derivatives for Integrin Targeting," Bioconjugate Chem., 2007, vol. 18, No. 6, pp. 1847-1854.
Tan, et al., "Enhanced secretion of adhesive recognition sequence containing hirudin III mutein in *E. coli*," Molecular Biotechnology, 2007, vol. 36, pp. 1-8, XP00254055.
Vandivier, et al., "Burying the Dead: The Impact of Failed Apoptotic Cell Removal (Efferocytosis) on Chronic Inflammatory Lung Disease," Chest, 2006, vol. 129, No. 6, pp. 1673-1682.
Search Report in International Application No. PCT/NL2010/050334 dated Aug. 3, 2010.

* cited by examiner

*Primary Examiner* — Elly-Gerald Stoica
(74) *Attorney, Agent, or Firm* — Gilberto M. Villacorta; Sunit Talapatra; Foley & Lardner LLP

(57) ABSTRACT

An Annexin A5 variant, comprising one or more RGD (Arg-Gly-Asp) sequences, is suitable for use in the treatment of a disease in mammals, including humans, wherein augmentation of phagocytosis is a desired effect of treatment. The Annexin A5 variant can e.g. be used in the treatment of chronic inflammatory diseases such as atherosclerotic plaque or in the treatment of COPD. At least one RGD sequence may substitute sequences of three amino acids within the range 1-19 or other regions of the amino acid sequences of Annexin A5; alternatively one or more RGD sequences may be part of an extension at the N-terminal side.

26 Claims, 1 Drawing Sheet

METHOD FOR ENHANCING PHAGOCYTOSIS OF PHOSPHATIDYLSERINE-EXPOSING CELLS

The invention pertains to means and methods for use in enhancing phagocytosis of phosphatidylserine-exposing cells, for example for the treatment of diseases that are characterized by chronic inflammation such as atherosclerosis and chronic autoimmune diseases such as systemic lupus erythematodes (SLE).

BACKGROUND

Apoptosis plays an important role in atherogenesis. A positive correlation exists between the number of apoptotic cells in the plaque and plaque instability. Phagocytosis of apoptotic cells is relevant to progression of atherosclerosis towards the unstable phenotype. Impaired phagocytosis is associated with accelerated progression of the atherosclerotic plaque towards the unstable phenotype. Atherosclerosis, hence, can be treated with methods that enhance phagocytosis of apoptotic cells.

Apoptotic cells expose phosphatidylserine (PS) at their cell surface. Annexin A5 (anxA5) binds to PS expressed on the apoptotic cell surface. AnxA5 bound to the apoptotic cell inhibits its phagocytosis by shielding the PS, which PS is recognized by the phagocyte as an 'eat me' signal (Kenis et al. *Exp. Cell Res.* 312 (2006) 719-726; and references cited therein).

Asano et al. *J. Exp. Med.* 200(4), 459-467 (2004) show that a milk fat globule mutant containing a point mutation in its RGD motif, inhibits phagocytosis of apoptotic cells and induces production of auto-antibodies upon injection in mice.

Bérat et al., *Biointerphases* 2(4), 165-172 (2007) describe a rat annexin A5 variant wherein Thr-163 is replaced by Cys, and a synthetic oligopeptide containing the RGD (arginine-glycine-aspartate) motif and a Cys residue is coupled to the Cys residue of the annexin mutant through a disulfide bond. Matrices of these annexin-RGD conjugates were found to promote adhesion of human saphenous vein endothelial cells. The authors suggest that these results may open cell-transporting techniques and the like. The annexin variants in which the RGD motif is attached to a central part of the molecule via a Cys-Cys (disulfide) bridge may have the disadvantage of insufficient stability in various environments.

DESCRIPTION OF THE INVENTION

This invention describes methods to enhance phagocytosis by using anxA5 variants that bind to PS on the apoptotic cell and activate phagocytes to engulf the apoptotic cell instead of inhibiting phagocytosis.

The tertiary structure of AnxA5 is arranged in four domains and an N-terminal tail at the concave side of the molecule connecting domain I and IV. The N-terminal tail is opposite to the convex side of the anxA5 molecule that harbours the $Ca^{2+}$/phospholipids binding sites. Hence, the concave side, and especially the N-terminal tail can be mutated and conjugated to different molecules (e.g. proteins or sugars) without interfering with the PS-binding capacity.

The anxA5 variants of the invention can thus carry a phagocytosis-inducing signal in or as an extension of its N-terminal tail or elsewhere at the concave side. The phagocytosis-inducing signal can be one or more, up to twenty RGD (arginine-glycine-aspartate) motifs. The variants can be anxA5 derivatives having an RGD motif in their N-terminal tail that activates integrin receptors of the phagocyte. Also anxA5 derivatives that carry the Fc-domain of IgG or parts thereof activate IgG-receptors of the phagocytes.

It is preferred that at least one or preferably each RGD motif is flanked by a neutral amino acid, in particular an amino acid selected from A, G, I, L, M, P, S, T and V.

The anxA5 variant of the invention contains at least one RGD motif within the Annexin chain, i.e. in the linear polypeptide chain constituting the annexin molecule. Thus, the RGD motif may be inserted within the annexin polypeptide chain or replace one or more, amino acids of the annexin molecule, or be attached to the N-terminal side of the annexin molecule. Thus, the annexin variant can be, and preferably is, produced by recombinant production using host cell which are transformed with the suitably modified DNA.

For example, the anxA5 variant of the invention can have one or more RGD sequences which substitute sequences of three amino acids in the concave surface of the anxA5 protein. The amino acids at the concave surface anxA5 are shown in italics in the sequence illustrated in Table 1 (SEQ ID No. 1) and include amino acid positions 1-19, 24, 28, 46-64, 86-89, 118-135, 150, 157-170, 202-219, 245-248, and 280-294. Thus the one or more RGD motifs are preferably located in the range 1-19, 46-64, 86-89, 118-135, 157-170, 203-219, 245-248 and 280-294, more preferably within the range 1-15, 46-58, 86-87, 118-134, (170), 245-248 and 280-294, indicated in bold italics in Table 1.

In particular, the anxA5 variants according to the invention have at least one RGD sequence which substitutes a sequence of three amino acids within the range 1-15, preferably within the range 1-10 of Table 1 (SEQ ID No. 1). Suitable examples of this embodiment include sequences 49-51 (substitution of QE by GD), 17-19 (A by G), 13-15 (GF by RG) by suitable replacement of the native sequences; in the latter two it is preferred that E at 16 is additionally substituted by a neutral amino acid. More suitable examples include 10-12 (DFP by RGD), 8-10 (VT by RG), 1-3 (AQV by RGD) and especially 5-7 (T by D).

TABLE 1

| Amino acid sequences of Human annexin A5 (without the original methionine). | |
|---|---|
| AQVLRGTVTD FPGFD<u>ERADA</u> <u>ETLRKAMK</u>GL GTDEESILTL | 40 |
| LTSR<u>S</u>NAQRQ EISAAFKT<u>LF</u> <u>GRDLLDDLKS</u> ELTGKFEKLI | 80 |
| VALMKPS<u>RLY</u> DAYELKHALK GAGTNEKVLT EIIASRTPEE | 120 |
| LRAIKQVYEE EYGS<u>SLEDDV</u> <u>VGDTSGYYQR</u> MLVVL<u>LQANR</u> | 160 |
| <u>DPDAGIDEA</u>Q VEQDAQALFQ AGELKWGTDE EKFITIFGTR | 200 |
| SV<u>SHLRKVFD</u> <u>KYMTISGFQI</u> EETIDRETSG NLEQLLLAVV | 240 |
| KSIRSIPAYL AETLYYAM<u>KG</u> <u>AGTDDH</u>TLIR VMVSRSEID<u>L</u> | 280 |
| FNIRKEFRKN FATSLYSMIK GDT<u>SGDYKKA</u> LLLLCGEDD | 319 |

Amino acids in italics are located on the concave side. Amino acids in bold italics are preferred amino acids for substitution at the concave side. Underlined regions are regions where amino acids can be substituted to inhibit internalization.

Alternatively or additionally, the anxA5 variant of the invention can have an extension at the N-terminus of the molecule, which extension contains one or more RGD sequences. The extension may for example be $X^1RGDX^2$ or $(X^1RGDX^2)_n$, wherein $X^1$ and $X^2$ can be any series of amino acids, the terminal ones being selected from A, G, I, L, M, P, S, T and V, preferably from A, G, P and S, and n can be from 1-19, preferably 2-9, e.g. 2 or 3. Preferably however, $X^1$ and $X^2$ each are one or two amino acids selected from A, G, I, L, M, P, S, T and V, preferably from A, G, P and S. Thus, an example is a sequence ARGD attached to the N-terminus (A) of the sequences of Table 1 (SEQ ID No.1). Further examples include RGDAARGD, RGDAARGDAARGDA (SEQ ID NO's 3, 4) etc. extended at the N-terminus of the anxA5 molecule. Thus, when the anxA5 variant contains more than one RGD sequence, each pair of RGD sequences is preferably separated by 1-3 amino acids selected from A, G, I, L, M, P, S, T and V.

amino acids containing a cyclic RGD that was rendered cyclic by disulfide bridge formation of flanking cysteine residues.

In an embodiment, a peptide of 3-20 amino acids containing RGD or cyclic RGD is coupled to annexin A5 or variant thereof through chemical coupling using standard techniques such as for example coupling to an amino group or a sulfhydryl group present in the annexin polypeptide. A preferred embodiment encompasses annexin A5 or variants thereof which have RGD or cyclic RGD containing peptides of 3-20 amino acids that are coupled to the concave side, especially the N-terminal side, of the annexin molecule.

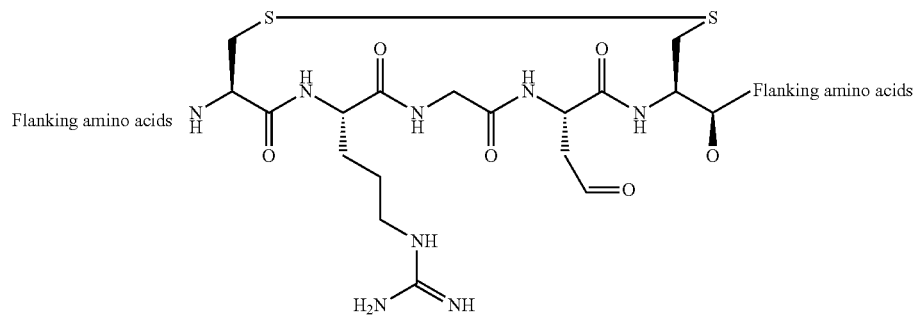 [SMILES: C[C@@H](O)[C@@H]1CSSC[C@H](N)C(=O)N[C@@H](CCCNC(=N)N)C(=O)NCC(=O)N[C@@H](CC=O)C(=O)N1]

As a further alternative, an anxA5 variant according to the invention may contain one or more RGD sequences which are attached to a cysteine residue which substitutes an amino acid at the N-terminal side of the annexin molecule, i.e. at one of the positions 1-19 of SEQ ID No.1 (Table 1). To this end, a cysteine residue is introduced at one of the above positions by methods known in the art, for example as described in WO 2006/003488, which is incorporated herein by reference. The one or more RGD motifs can be coupled to the sulfhydryl group of the cysteine residue e.g. by a linker. The linker can e.g. be selected from maleimide containing groups, halogen containing groups, an isothiocyanate, an isocyanate, an imido ester, and a succinimidyl ester group, to which e.g. ethylene diamine is bound. Thus in particular, the linker contains an amino group, to which the RGD motif, or $X^1RGDX^2$ or $(X^1RGDX^2)_n$ motifs (see above) can be bound.

It is preferred that in such Cys derivatives, any cysteine originally present at a non-concave position, in particular at a site buried within the molecule as indicated by underlining in Table 1, is substituted by another amino acid, such as an alanine or serine residue; see WO 2006/003488 and WO 2007/069895. This applies specifically to the cysteine residue originally present at position 315 of the anxA5 molecule. Hence, an anxA5 variant in which Cys-315 has been replaced by another amino acid, or has been deleted, is preferred.

Alternatively or additionally to a straight RGD-containing sequence, the anxA5 variant may contain a cyclic RGD sequence or a plurality thereof. Such cyclic RGD sequence may have the cyclic structure c-$X^3$RGD, wherein $X^3$ may represent one, two or three amino acids, other than R and D, which contain one linking amino acid such as K, N, Q, or a triazole-containing or other synthetic amino acid allowing coupling to the anxA5 molecule, e.g. to a cysteine residue thereof. The synthesis of cyclic RGD derivatives is described e.g. by Kuijpers et al. *Bioconjugate Chem.* 2007, 18, 1847-1854 and references cited therein. RGD can be made cyclic for example by flanking the RGD motif with a cysteine at both sides and oxidising the cysteines to form a disulfide bridge. The formula below shows an example of a peptide of 5-20

In a particular embodiment, the annexin variant according to the invention containing the RGD motif is further modified so as to inhibit internalisation into a cell. In such a variant, one or more amino acids within the helices involved in the intermolecular interactions between annexin molecules are replaced by different amino acids. These replacement amino acids are located at positions 16-29, 59-74, 88-102, 135-145, 156-169, 202-231, 259-266, and 305-317 in annexin A5, and these positions are underlined in Table 1 (SEQ ID No. 1). Where the annexin variant contains one or more of these modifications, the feature of the annexin not being internalised into a cell will be fulfilled. Thus, the invention also comprises an annexin variant that a) contains one or more RGD sequences and b) contains one or more of the amino acid modifications as described herein. Such annexin derivatives are described in WO 2007/069895, which is incorporated herein by reference.

Preferred modifications inhibiting internalisation are substitutions, especially substitutions of polar amino acids by non-polar amino acids. Thus, preferred amino acids for substitution include arginine (R), lysine (K), aspartate (D), glutamate (E), asparagine (N) and glutamine (Q). They may be substituted e.g. by glycine (G), alanine (A), proline (P), serine (S), threonine (T) and valine (V), especially A or G, or by a non-polar amino acid that is located in the corresponding position of another annexin (cf. Table 1). Suitable examples of substituted amino acids include E21, K25 (e.g. by G, T), R62 (e.g. G, A), D63 (e.g. G, A, P), K69, D91, K96, H97, K100, E137 (e.g. A, G, V), D138, D139, N159 (e.g. A, G, S), R160, R206, K207, Q219, D225, 8226, D264, K308, K309. It is preferred in this particular embodiment, to have at least two, or even at least three, substitutions in different regions, for example R62A+E137G, or K69A+K100A+N159S etc., in order to further decrease the trimerisation of the annexin at the site of the cell.

In the embodiment described above, wherein the anxA5 variant further contains a cysteine residue at one of the concave positions 1-19, 24, 28, 46-64, 86-89, 118-135, 149-150, 157-170, 203-219, 245-248 and 280-294, said cysteine allows coupling to one or more RGD motifs as described above.

In molecules which already contain one or more RGD motifs, e.g. by suitable substitution or extension, said cysteine residue can be a suitable function for coupling to a diagnostic or therapeutic molecule, e.g. as described in WO 2006/003488. Suitable diagnostics are optical probes such as for example fluorochromes in the visible, near infrared and infrared region and nuclear probes as for example $^{99m}$Tc, $^{68}$Ga, $^{64}$Cu, $^{111}$In, $^{124}$I and $^{18}$F. Suitable therapeutic agents are compounds that inhibit protease activity such as for example chemical compounds or peptides that inhibit matrix metalloproteases. Other suitable therapeutics are compounds that inhibit platelet activation and blood coagulation such as for example heparin or low molecular weight derivatives thereof. Suitable therapeutic agents are also radioisotopes that have beta-emission such as for example $^{186}$Re and $^{90}$Y, The examples serve the purpose of indication and do not imply a limitation of possibilities.

As an alternative means for providing the annexin variant with a diagnostic or therapeutic metal species, the Annexin A5 variant of the invention may advantageously further comprise from 2 up to 10 amino acid residues at its N-terminus, allowing association with metal diagnostics or therapeutics. Such amino acids are especially histidine residues, at least two of said histidine residues being adjacent or separated by no more than one other amino acid. The metal diagnostic or therapeutic can e.g. be a radionuclide, such as gallium 67, gallium 68, indium 111, technetium 99m, rhenium 188, Copper 64 and Tin 117m. An example is an annexin variant of the invention, e.g. carrying an RGD motif in or attached to its region of amino acids 1-15, which further containing 3-6 histidine residues attached to N-terminal side of the alanine at position 1, to which one of the metals is associated. Annexin variants containing histidine residues and their metal complexes and uses are described in WO 2010/024673.

Apart from the substitutions and additions described above, the anxA5 variant of the present invention may contain further substitutions, deletions or insertions to the sequence as depicted in Table 1 (SEQ ID No 1). Such substitutions, deletions or insertions may especially be conservative substitutions as occurring when comparing the human anx5 sequence of Table 1 with that of other animal species, e.g. rat, mouse, monkey, cow or other, or with that of other annexins, such as anxA1, anxA4, anxA8, anxA9, etc., which sequences are readily accessible (e.g. through http://www.structuralchemistry.org/annexins/seq/search.php).

However, it is preferred that, apart from extensions at the N-terminal side or side-chains described above, the amino acid sequence of the anxA5 variant of the invention has at least 80% amino acid identity and at least 90% amino acid similarity with the sequence of SEQ ID NO. 1, more preferably at least 90% amino acid identity and at least 95% amino acid similarity, most preferably 95-99.7% amino acid identity and especially 97-99.7% amino acid similarity. It is preferred that the anxA5 variant is based on human anxA5, i.e. has the above degrees of identity with the human sequence (Table 1, SEQ ID NO. 1), and in particular so in the convex areas (the non-underlined parts of Table 1), especially an amino acid identity in the region 29-45 of at least 90% (at least 15 out of 17), more preferably at least 95% (16/17), most preferably 100% (all 17 amino acids identical).

The anxA5 variant described herein can be used in pharmaceutical compositions, methods, kits, and devices as also described herein. An embodiment of the invention relates to a method for treating a subject in need of treatment of a disease that includes administering a therapeutic composition of the variant described above which optionally contains at least one pharmaceutically acceptable excipient. Administration and dosage of a therapeutic composition can vary between patients and are well known in the medical art. The preferred dosage will depend upon the disease being treated, the therapeutic compound or mix of compounds, and the patient among other factors. Possible delivery routes of the complexes are subcutaneous, intramuscular, intra-peritoneal and intravenous administration. Those of skill in the art will know of other delivery routes. Complexes can administered as a bolus or continuously per infusion covering a longer period of time. Doses range from 0.1 µg/kg to 100 mg/kg (anxA variant over body weight) in diagnostic procedures and 1 µg/kg to 100 mg/kg in therapeutic procedures. Preferred ranges are 1 µg/kg-1 mg/kg (diagnostic) and 5 µg/kg-50 mg/kg (therapeutic).

The anxA5 variant as described above is suitable for use in stimulating phagocytosis of cells that expose phosphatidylserine on their surface, in particular apoptotic cells. Thus, the anxA5 variant can be used in the treatment of a disease in mammals, including humans, which comprises the augmentation of phagocytosis as a desired effect of treatment. Such diseases include diseases associated with atherosclerotic plaque and especially the advanced atherosclerotic plaque that carries an increased risk of vascular rupturing such as plaques indicated by AHA classification type II, III, IV, V and IV. The effect of the treatment will be a slow-down of plaque progression and concomitantly a reduction of risk of rupturing, The term efferocytosis (from effero=to bury, to carry to the grave) was coined by Henson et al. for the phagocytic removal of apoptotic cells (Gardai S J, McPhillips K A, Frasch S C, Janssen W J, Starefeldt A, Murphy-Ullrich J E, et al., Cell 2005; 123: 321-334). Chronic obstructive pulmonary disease (COPD) is associated with defective efferocytosis in humans and animal models (S. Hodge et al, Am. J. Respiratory Cell and Molecular Biology, vol. 37, pp 748-755, 2007; Vandivier et al., Chest, June 2006 vol. 129, No. 6, 1673-1682). Apoptotic cells can undergo secondary necrosis and thereby perpetuate inflammation. Low dose administrations of the macrolide antibiotic Azithromycin to patients with COPD have been used to improve phagocytic ability of Alveolar Macrophages as a novel approach to supplement existing therapies (Hodge et al., American Journal of Respiratory and Critical Care Medicine, Vol. 178, pp 139-148, 2008). The anxA5 variant will therefore be useful in the treatment of COPD by stimulating the removal of apoptotic cells.

The anxA5 variant according to the invention can be used in a method for stimulating phagocytosis of cells that expose phosphatidylserine on their surface, which method comprises administering to a subject in need thereof the anxA5 variant, in a pharmaceutically acceptable composition. Such composition may be administered through intravenous infusion of a solution or through inhalation of a pharmaceutical aerosol delivery formulation.

The anxA5 variants of the invention are particularly useful for treating conditions in which phagocytosis is defective and inflammatory responses play a central role. Hence, the invention relates to methods of treatment of chronic inflammatory diseases such as arthritis, atherosclerosis, chronic obstructive pulmonary diseases (COPD), including chronic bronchitis and emphysema, and chronic autoimmune diseases such as systemic lupus erythematodes (SLE), inflammatory bowel diseases, including Crohn's disease, ulcerative colitis and celiac disease, psoriasis, rheumatoid arthritis, multiple sclerosis, myasthenia gravis, Sjögren's syndrome, etc.

EXAMPLES

AnxA5 variants are made that carry a phagocytosis inducing signal in the N-terminal tail. The variants can further contain a cysteine residue in the N-terminal tail either as part of an extension of the tail, or within the tail by replacement of glutamine at position 2.

Example 1

Production of Annexin A5 Variant Having an RGD Motif

The human annexin A5 cDNA was prepared from a white blood cell cDNA library from a healthy volunteer with standard techniques known in the art. The cDNA sequence encoded the amino acid sequence presented in Table 1. Primers were designed to mutate annexin A5 by PCR techniques such that the resulting cDNA encoded the amino acid sequence of Table 1 with the exception of the substitution of T (Thr), encoded by ACN (N=T, C, A or G), at position 7 by D (Asp), encoded by GAY (Y=T or C). The variant is denoted as A5 T7D, and its sequence is represented in SEQ ID No.2.

The annexin A5-T7D cDNA was cloned into a bacterial expression vector with standard techniques known in the art. *E. coli* transformed with the resulting bacterial expression vectors were grown in a fermentor. The annexin A5-T7D variant produced by the bacteria was isolated and purified from *E. coli* lysates with standard chromatography techniques known to persons skilled in the art.

The purified annexin A5-T7D variant appeared as a homogenous band with an apparent molecular weight of around 34 kDa on SDS-PAGE and exhibited full calcium-dependent phosphatidylserine binding activity as measured by plasmon surface resonance technique using the BiaCore system.

Example 2

Effect of Annexin A5 Variant Having an RGD Motif

Figure 1A:
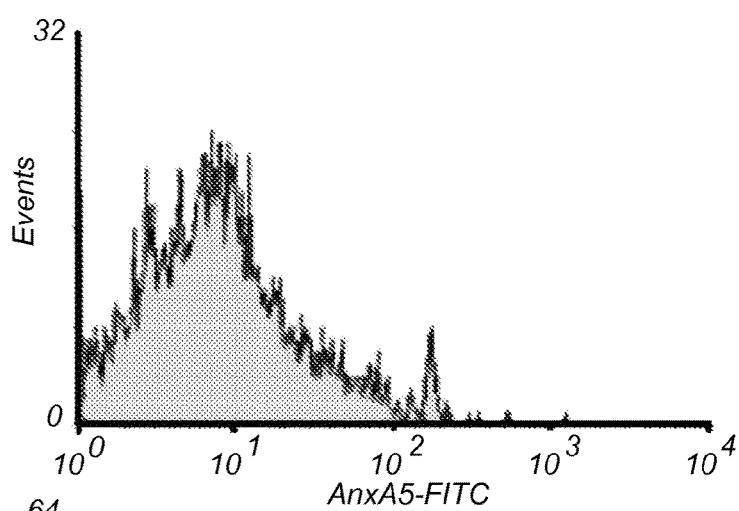
FIG. 1A shows a histogram of the flow cytometric analysis of MCF-7 cells incubated with anxA5-FITC.
Figure 1B:
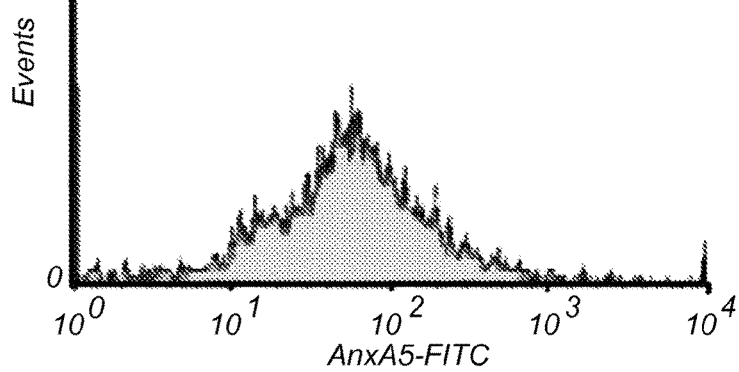
FIG. 1B shows the histogram of MCF-7 cells incubated with RGD-anxA5-FITC produced according to Example 1. Incubation of MCF-7 cells with RGD-anxA5-FITC resulted in increased binding of RGD-anxA5-F to MCF-7 cells.

In order to demonstrate that the T7D substitution results in a functional RGD motif on anxA5 MCF-7 cells (FIG. 1) and THP-1 cells were incubated with fluorescein labeled anxA5 or fluorescein labeled T7D anxA5. MCF-7 cells and THP-1 cells express $\alpha_v\beta_3$ and $\alpha_v\beta_5$. Preliminary data confirm that incorporation of RGD (Arginine-Glycine-Aspartic-acid) into the N-terminal tail of anxA5 increases the binding to $\alpha_v\beta_3$ and $\alpha_v\beta_5$ expressing cells, indicating that RGD is exposed for interaction with integrin-receptor (see FIG. 1).

Further, the effect of anxA5 or T7D anxA5 on phagocytosis of apoptotic cells was studied by addition of anxA5 or T7D anxA5 to a mixture of THP-1 cells (phagocytes) and anti-Fas stimulated Jurkat cells (apoptotic cells). AnxA5 inhibits phagocytosis of apoptotic cells likely by shielding the expressed PS on the apoptotic surface. By introducing RGD into the N-terminal tail of anxA5 inhibition is reversed into potentiating of phagocytosis (see FIG. 2). Therefore the overall conclusion of the preliminary data is that RGD in the N-terminal tail of anxA5 stimulates phagocytosis of apoptotic cells likely through activation of integrin receptors of the phagocyte.

Figure 2:
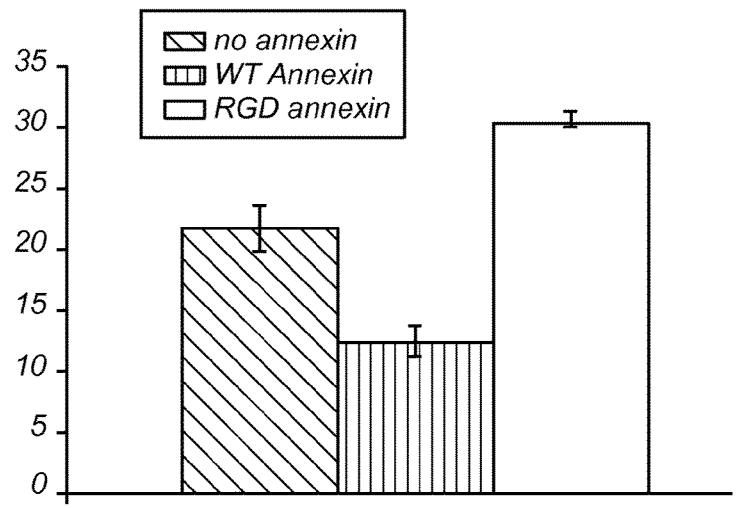
FIG. 2 shows that AnxA5 inhibits and RGD-anxA5 stimulates phagocytosis of apoptotic Jurkat cells by differentiated THP-1 cells.

FIG. 2 shows that AnxA5 inhibits and RGD-anxA5 stimulates phagocytosis of apoptotic Jurkat cells by differentiated THP-1 cells.

Example 3

Production of Annexin A5 Variant Having an RGD Motif and a Cys Residue at the N-Terminus Human annexin A5 cDNA was mutated in the manner as described in example 1, with the further substitution of Q (Gln), encoded by GAR (R=A or G), at position 2 by C (Cys), encoded by TGY (Y=T or C). The variant is denoted as A5 Q2C T7D.

The cysteine of this variant can be used for coupling diagnostics of therapeutics The variant can be further mutated by substitution of Cys-315 by e.g. Ser or Ala.

---

The invention claimed is:

1. An isolated variant of Annexin A5, wherein at least one set of three consecutive amino acids at positions 1-19 of SEQ ID NO: 1 are replaced with an Arg-Gly-Asp (RGD) amino acid sequence, wherein at least one RGD sequence is located on an amino acid sequence extension at the N-terminus of the Annexin A5 molecule.

2. The Annexin A5 variant according to claim 1, comprising more than one RGD sequence, wherein each pair of RGD sequence is separated by 1-3 amino acids selected from A, G, I, L, M, P, S, T and V.

3. The Annexin A5 variant according to claim 1, wherein at least one RGD sequence replaces three amino acids within the range 1-15 of SEQ ID No. 1.

4. The Annexin A5 variant according to claim 3, wherein at least one RGD sequence replaces three amino acids within the range 1-10 of SEQ ID No. 1.

5. The Annexin A5 variant according to claim 1, further comprising at least one additional RGD sequence as part of a cyclic sequence comprising 3-20 amino acids.

6. The Annexin A5 variant according to claim 1, further comprising a cysteine residue at one of the positions 1-19 of SEQ ID NO: 1, said cysteine residue optionally being coupled to a diagnostic or therapeutic molecule.

7. A composition comprising an Annexin A5 variant according to claim 1 and a pharmaceutically acceptable excipient, carrier, and/or diluent.

8. An isolated variant of Annexin A5, wherein at least one set of three consecutive amino acids at positions 1-15 of SEQ ID NO: 1 is replaced with an Arg-Gly-Asp (RGD) amino acid sequence.

9. The Annexin A5 variant according to claim 8, comprising more than one RGD sequence, wherein each pair of RGD sequence is separated by 1-3 amino acids selected from A, G, I, L, M, P, S, T and V.

10. The Annexin A5 variant according to claim 8, wherein at least one RGD sequence replaces three amino acids within the range 1-10 of SEQ ID NO: 1.

11. The Annexin A5 variant according to claim 8, further comprising a cysteine residue at one of the positions 1-15 of SEQ ID NO: 1, said cysteine residue optionally being coupled to a diagnostic or therapeutic molecule.

12. A composition comprising an Annexin A5 variant according to claim 8 and a pharmaceutically acceptable excipient, carrier, and/or diluent.

13. A method of stimulating phagocytosis of cells expressing surface phosphatidylserine, comprising administering to a subject an in need thereof an effective amount of Annexin A5 variant according to claim 8.

14. The method of treating a mammal, comprising administering to a mammal in need thereof a therapeutically effective amount of a composition comprising an Annexin A5 variant according to claim 8 and a pharmaceutically acceptable excipient, carrier, and/or diluent, wherein the administration augments phagocytosis of apoptotic cells.

15. The method according to claim 14, wherein the mammal is a human.

16. The method of claim 14, wherein the mammal is suffering from a chronic inflammatory disease.

17. The method according to claim 16, wherein the chronic inflammatory disease comprises a chronic autoimmune disease.

18. A method of treating from a chronic inflammatory disease, atherosclerotic plaque, COPD, systemic lupus erythematodes, and/or rheumatoid arthritis, comprising administering to a mammal in need thereof a therapeutically effective amount of a composition comprising an Annexin A5 variant according to claim 8 and a pharmaceutically acceptable excipient, carrier, and/or diluent.

19. The method according to claim 14, wherein the mammal is a human.

20. An isolated variant of Annexin A5, wherein at least one set of three consecutive amino acids at positions 1-19 are replaced with an Arg-Gly-Asp (RGD) amino acid sequence, and comprising at least one additional RGD sequence as part of a cyclic sequence comprising 3-20 amino acids.

21. The Annexin A5 variant according to claim 20, further comprising a cysteine residue at one of the positions 1-19 SEQ ID NO: 1, said cysteine residue optionally being coupled to a diagnostic or therapeutic molecule.

22. The Annexin A5 variant according to claim 20, which further comprises 2 to 10 histidine residues at the N-terminus, at least two of said histidine residues being adjacent or separated by no more than one other amino acid, and optionally being bound to a radionuclide.

23. A composition comprising an Annexin A5 variant according to claim 20 and a pharmaceutically acceptable excipient, carrier, and/or diluent.

24. An isolated variant of Annexin A5, wherein at least one set of three consecutive amino acids at positions 1-19 SEQ ID NO: 1 are replaced with an Arg-Gly-Asp (RGD) amino acid sequence, and comprising 2 to 10 histidine residues at the N-terminus, at least two of said histidine residues being adjacent or separated by no more than one other amino acid, and optionally being bound to a radionuclide.

25. The Annexin A5 variant according to claim 24, further comprising a cysteine residue at one of the positions 1-19 SEQ ID NO: 1, said cysteine residue optionally being coupled to a diagnostic or therapeutic molecule.

26. A composition comprising an Annexin A5 variant according to claim 24 and a pharmaceutically acceptable excipient, carrier, and/or diluent.

* * * * *

SEQUENCE LISTING

```
<160> NUMBER OF SEQ ID NOS: 2

<210> SEQ ID NO 1
<211> LENGTH: 319
<212> TYPE: PRT
<213> ORGANISM: Homo sapiens

<400> SEQUENCE: 1

Ala Gln Val Leu Arg Gly Thr Val Thr Asp Phe Pro Gly Phe Asp Glu
1               5                   10                  15

Arg Ala Asp Ala Glu Thr Leu Arg Lys Ala Met Lys Gly Leu Gly Thr
            20                  25                  30

Asp Glu Glu Ser Ile Leu Thr Leu Leu Thr Ser Arg Ser Asn Ala Gln
        35                  40                  45

Arg Gln Glu Ile Ser Ala Ala Phe Lys Thr Leu Phe Gly Arg Asp Leu
    50                  55                  60
```

-continued

```
Leu Asp Asp Leu Lys Ser Glu Leu Thr Gly Lys Phe Glu Lys Leu Ile
 65                  70                  75                  80

Val Ala Leu Met Lys Pro Ser Arg Leu Tyr Asp Ala Tyr Glu Leu Lys
                 85                  90                  95

His Ala Leu Lys Gly Ala Gly Thr Asn Glu Lys Val Leu Thr Glu Ile
            100                 105                 110

Ile Ala Ser Arg Thr Pro Glu Glu Leu Arg Ala Ile Lys Gln Val Tyr
        115                 120                 125

Glu Glu Glu Tyr Gly Ser Ser Leu Glu Asp Asp Val Val Gly Asp Thr
    130                 135                 140

Ser Gly Tyr Tyr Gln Arg Met Leu Val Val Leu Leu Gln Ala Asn Arg
145                 150                 155                 160

Asp Pro Asp Ala Gly Ile Asp Glu Ala Gln Val Glu Gln Asp Ala Gln
                165                 170                 175

Ala Leu Phe Gln Ala Gly Glu Leu Lys Trp Gly Thr Asp Glu Glu Lys
            180                 185                 190

Phe Ile Thr Ile Phe Gly Thr Arg Ser Val Ser His Leu Arg Lys Val
        195                 200                 205

Phe Asp Lys Tyr Met Thr Ile Ser Gly Phe Gln Ile Glu Glu Thr Ile
    210                 215                 220

Asp Arg Glu Thr Ser Gly Asn Leu Glu Gln Leu Leu Leu Ala Val Val
225                 230                 235                 240

Lys Ser Ile Arg Ser Ile Pro Ala Tyr Leu Ala Glu Thr Leu Tyr Tyr
                245                 250                 255

Ala Met Lys Gly Ala Gly Thr Asp Asp His Thr Leu Ile Arg Val Met
            260                 265                 270

Val Ser Arg Ser Glu Ile Asp Leu Phe Asn Ile Arg Lys Glu Phe Arg
        275                 280                 285

Lys Asn Phe Ala Thr Ser Leu Tyr Ser Met Ile Lys Gly Asp Thr Ser
    290                 295                 300

Gly Asp Tyr Lys Lys Ala Leu Leu Leu Leu Cys Gly Glu Asp Asp
305                 310                 315
```

<210> SEQ ID NO 2
<211> LENGTH: 319
<212> TYPE: PRT
<213> ORGANISM: Artificial
<220> FEATURE:
<223> OTHER INFORMATION: T7D mutant of human annexin 5

<400> SEQUENCE: 2

```
Ala Gln Val Leu Arg Gly Asp Val Thr Asp Phe Pro Gly Phe Asp Glu
  1               5                  10                  15

Arg Ala Asp Ala Glu Thr Leu Arg Lys Ala Met Lys Gly Leu Gly Thr
                 20                  25                  30

Asp Glu Glu Ser Ile Leu Thr Leu Leu Thr Ser Arg Ser Asn Ala Gln
             35                  40                  45

Arg Gln Glu Ile Ser Ala Ala Phe Lys Thr Leu Phe Gly Arg Asp Leu
         50                  55                  60

Leu Asp Asp Leu Lys Ser Glu Leu Thr Gly Lys Phe Glu Lys Leu Ile
 65                  70                  75                  80

Val Ala Leu Met Lys Pro Ser Arg Leu Tyr Asp Ala Tyr Glu Leu Lys
                 85                  90                  95

His Ala Leu Lys Gly Ala Gly Thr Asn Glu Lys Val Leu Thr Glu Ile
            100                 105                 110

Ile Ala Ser Arg Thr Pro Glu Glu Leu Arg Ala Ile Lys Gln Val Tyr
```

-continued

```
                        115                 120                 125
Glu Glu Glu Tyr Gly Ser Ser Leu Glu Asp Asp Val Val Gly Asp Thr
            130                 135                 140
Ser Gly Tyr Tyr Gln Arg Met Leu Val Val Leu Leu Gln Ala Asn Arg
145                 150                 155                 160
Asp Pro Asp Ala Gly Ile Asp Glu Ala Gln Val Glu Gln Asp Ala Gln
                165                 170                 175
Ala Leu Phe Gln Ala Gly Glu Leu Lys Trp Gly Thr Asp Glu Glu Lys
            180                 185                 190
Phe Ile Thr Ile Phe Gly Thr Arg Ser Val Ser His Leu Arg Lys Val
            195                 200                 205
Phe Asp Lys Tyr Met Thr Ile Ser Gly Phe Gln Ile Glu Glu Thr Ile
        210                 215                 220
Asp Arg Glu Thr Ser Gly Asn Leu Glu Gln Leu Leu Leu Ala Val Val
225                 230                 235                 240
Lys Ser Ile Arg Ser Ile Pro Ala Tyr Leu Ala Glu Thr Leu Tyr Tyr
                245                 250                 255
Ala Met Lys Gly Ala Gly Thr Asp Asp His Thr Leu Ile Arg Val Met
            260                 265                 270
Val Ser Arg Ser Glu Ile Asp Leu Phe Asn Ile Arg Lys Glu Phe Arg
        275                 280                 285
Lys Asn Phe Ala Thr Ser Leu Tyr Ser Met Ile Lys Gly Asp Thr Ser
        290                 295                 300
Gly Asp Tyr Lys Lys Ala Leu Leu Leu Leu Cys Gly Glu Asp Asp
305                 310                 315
```